(12) United States Patent
Paparatto et al.

(10) Patent No.: US 6,888,013 B2
(45) Date of Patent: May 3, 2005

(54) INTEGRATED PROCESS FOR THE PREPARATION OF OLEFIN OXIDES

(75) Inventors: Giuseppe Paparatto, Balsamo-Milan (IT); Anna Forlin, Vigonza-Padova (IT); Giordano De Alberti, Besnate-Varese (IT); Rino D'Aloisio, Novara (IT); Paolo Tegon, Oriago-Venezia (IT)

(73) Assignee: Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 10/343,832

(22) PCT Filed: Aug. 6, 2001

(86) PCT No.: PCT/EP01/09076
§ 371 (c)(1),
(2), (4) Date: Sep. 25, 2003

(87) PCT Pub. No.: WO02/14299
PCT Pub. Date: Feb. 21, 2002

(65) Prior Publication Data
US 2004/0054200 A1 Mar. 18, 2004

(30) Foreign Application Priority Data
Aug. 11, 2000 (IT) .................................... MI2000A1884

(51) Int. Cl.$^7$ ............................................. C07D 301/06
(52) U.S. Cl. ....................................... 549/532; 549/523
(58) Field of Search .................................. 549/523, 532

(56) References Cited

U.S. PATENT DOCUMENTS 5,384,418 A  1/1995  Zajacek et al.
5,912,367 A  6/1999  Chang
6,541,648 B1  4/2003  Paparatto et al.

FOREIGN PATENT DOCUMENTS

EP  0 568 337  11/1993
EP  1 074 548  2/2001

*Primary Examiner*—Amelia A. Owens
(74) *Attorney, Agent, or Firm*—Oblon, Spivak, McClelland, Maier & Neustadt, P.C.

(57) ABSTRACT

The present invention relates to an integrated process for the preparation in continuous of epoxides which comprises: (a) preparing an alcoholic or hydro-alcoholic solution of hydrogen peroxide in a concentration of over 3% by weight, using a gaseous stream containing hydrogen, oxygen and an inert gas, in the presence of a bimetallic catalyst based on palladium and platinum as active components; (b) putting the alcoholic or hydro-alcoholic solution of hydrogen peroxide obtained in step (a) in contact with an olefin and a buffering agent, in the presence of an epoxidation catalyst suspended in the reaction solvent, in order to obtain a reaction mixture containing the epoxide corresponding to the olefin, water and alcoholic solvent; (c) treating the alcoholic stream leaving step (b), after separation of the epoxide, in order to eliminate the nitrogenated compounds present; (d) feeding the alcoholic solvent obtained in (c) to step (a). The process may comprise a further step (e), wherein the raw hydro-alcoholic mixture of the flash column bottom, is used, when necessary, for diluting the alcoholic or hydro-alcoholic solution of hydrogen peroxide obtained in step (a) to the value required by the epoxidation plant. The process operates under high safety conditions and with a high overall efficiency, in terms of productivity and selectivity.

91 Claims, 1 Drawing Sheet

Fig.1

INTEGRATED PROCESS FOR THE PREPARATION OF OLEFIN OXIDES

The present invention relates to an integrated process for the preparation in continuous of epoxides by the direct oxidation of an olefin with hydrogen peroxide.

More specifically, the present invention relates to an integrated process for the preparation in continuous of propylene oxide consisting in the production of an alcoholic or hydro-alcoholic solution of hydrogen peroxide by the reaction between hydrogen and oxygen in the presence of a bimetallic catalyst based on palladium or platinum as active components, feeding said solution to an epoxidation process of propylene in the presence of an epoxidation catalyst, and feeding the recycled alcoholic solvent leaving the epoxidation plant, suitably pretreated, to the hydrogen peroxide production plant. The process may comprise a further step (e), in which the raw hydro-alcoholic mixture of the flash column bottom, is used, when necessary, for diluting the alcoholic or hydro-alcoholic solution of hydrogen peroxide obtained in step (a) to the value required by the epoxidation plant.

Epoxides, or olefin oxides, are intermediates which can be used for the preparation of a wide variety of compounds. For example, epoxides can be used for the production of glycols, condensation polymers such as polyesters or for the preparation of intermediates used in the synthesis of polyurethane foams, elastomers, seals and similar products.

Current technologies adopted on an industrial scale for the production of propylene oxide (PO) are based on processes via chlorohydrin and processes via indirect oxidation with hydroperoxides as oxygen source.

In particular, the commercialized chlorohydrin process involves the synthesis of propylene chlorohydrin (PCH) and subsequent dehydrohalogenation of PCH to propylene oxide (PO).

This process however has the following disadvantages:
  the production of high quantities of aqueous effluents (40–60 Kg/kg of PO) containing sodium or calcium chlorides;
  the coproduction of chlorinated organic products which, depending on their end-use, must undergo suitable treatment.

Processes via oxidation preferably use ter butyl hydroperoxide and ethylbenzene hydroperoxide as hydroperoxides.

These processes cause the formation of a higher quantity of co-products of commercial interest with respect to PO. For example, the process via ter butyl hydroperoxide co-produces 2.5–3.5 Kg of ter butyl alcohol per Kg of PO, whereas that via ethylbenzene hydroperoxide co-produces 2.2–2.5 Kg of styrene per Kg of PO.

The presence of these co-products can be of little advantage if the request for PO and the respective co-products is not suitably balanced. For example, when the demand for styrene or MTBE, obtained from ter butyl alcohol, is high, the economics of this process are competitive with those of the process via chlorohydrin, otherwise these processes are not economic.

Other synthetic techniques for the indirect oxidation of propylene involve the use of hydrogen peroxide and essentially consist in:
1) synthesis of hydrogen peroxide; and
2) its use in the epoxidation process of propylene to propylene oxide.

Aqueous solutions of $H_2O_2$ are typically obtained industrially by means of a complex two-step process. In this process a solution of anthraquinone, such as butylanthraquinone or ethylanthraquinone, in an organic medium immiscible with water, is first hydrogenated and then oxidized with air to produce $H_2O_2$ which is subsequently extracted in aqueous phase. This process is onerous due to the high costs deriving from the investment necessary for setting up the complex production unit, the necessity of separating and disposing of the by-products generated during the oxidation phase, and purifying and reintegrating the anthraquinone solution before its re-use.

A second method for the production of hydrogen peroxide comprises the use of secondary alcohols such as isopropanol and methylbenzylalcohol (U.S. Pat. No. 2,871,102, EP-378,388) or high-boiling secondary alcohols such as diaryl methanol (U.S. Pat. No. 4,303,632) with oxygen.

These known processes, however, substantially suffer from disadvantages deriving from the necessity of operating at high reaction temperatures (generally ranging from 100 to 180° C.), the partial oxidation of the ketone which is formed as main co-product, the necessity of using a hydrogen peroxide stabilizer (orthophosphoric acid or sodium pyrophosphate).

Furthermore, these processes are complicated by the necessity of separating and recovering the ketone and by-products from the reaction mixture before using the hydrogen peroxide solution in a subsequent epoxidation process.

Another method for the production of hydrogen peroxide, which seems attractive from a technical and economic point of view, is based on the direct synthesis of hydrogen peroxide from $H_2$ and $O_2$.

These processes generally use a catalytic system consisting of a noble metal, particularly metals of the platinum group or their mixtures, in the form of salts or as supported metals, by reacting the two gases in a solvent consisting of an aqueous medium or an aqueous-organic medium.

The industrial embodiment of these processes however has proved to be difficult for the following reasons:
A) the use of mixtures of $H_2$ and $O_2$ in concentrations falling within the explosivity range, as the mixture becomes explosive when the concentration of $H_2$ exceeds a value which, in relation to the pressure and concentration of $O_2$, varies from 4.5 to 6% by volume;
B) even when operating outside the explosivity range of $H_2$—$O_2$ mixtures, the use of high concentrations of $O_2$ is risky to handle and has a limited compatibility with the presence of flammable organic solvent mediums;
C) the use in the reaction medium of high concentrations of promoters, for example acid promoters, halogenated products and/or other additives, makes the catalytic system or $H_2O_2$ solution unstable. This makes it necessary to add stabilizers, with onerous purification operations of the $H_2O_2$ solution before its use;
D) low productivity and selectivity of the reaction and the production of $H_2O_2$ solutions which are too dilute for economic industrial exploitation;
E) poor stability of the catalytic system under the reaction conditions.

Patent application EP-812836, for example, describes a process for the preparation of propylene oxide which consists in reacting hydrogen and oxygen in the presence of a catalytic system based on supported palladium, in a hydro-alcoholic medium and using the hydro-alcoholic mixture of hydrogen peroxide thus obtained in the epoxidation process.

The illustrative examples of this document describe the production of hydro-alcoholic solutions containing $H_2O_2$ in concentrations ranging from 0.15 to 0.39% by weight. Using these solutions in the subsequent epoxidation reaction, after 1 hour, hydrogen peroxide conversions equal to 99% and 65% respectively, are obtained, with a selectivity to propylene oxide ranging from 70% to 95%, i.e. with a maximum yield to PO of 70%.

This process does not seem to be of industrial interest for the following reasons:

A) The use, in the reaction medium for the production of hydrogen peroxide, of high concentrations of promoters, for example acid promoters, halogenated products and/or other additives, makes it necessary to add considerable quantities of neutralizers before its use in the subsequent epoxidation process;
B) overall low process concentration, productivity and selectivity. This requires the use of high reaction volumes in both steps of the integrated process;
C) Production of a high stream of waste products to be disposed of in the epoxidation process;
D) The use of diluted hydro-alcoholic solutions of hydrogen peroxide implies the production of a stream of alcoholic distillate whose entity makes the process rather un-economic.

The Applicant has now found that by using a well defined group of metallic catalysts and operating conditions in the initial reaction between hydrogen and oxygen, by suitably treating the recycled alcoholic solvent leaving the epoxidation plant before being fed to the hydrogen peroxide production plant, and by using the raw hydro-alcoholic mixture of the flash column bottom, when necessary, to dilute the hydro-alcoholic solution of hydrogen peroxide obtained in step (a) to the value required by the epoxidation plant, an overall high process efficiency is obtained in terms of productivity and selectivity.

In particular, when operating according to the process of the present invention, the following advantages are obtained:

reduction in waste products in the epoxidation plant;
reduction in the volume of solvent to be distilled in the epoxidation reaction plant;
high stability of the catalysts used in the two reactions;
reduction in the reaction volumes;
high degree of purity of the epoxides.

In accordance with this, the objective of the present invention relates to an integrated process for the preparation in continuous of epoxides by the direct oxidation of an olefin with hydrogen peroxide which comprises:

(a) preparing an alcoholic or hydro-alcoholic solution of hydrogen peroxide in a concentration of over 3% by weight, using a gaseous stream containing hydrogen, oxygen and an inert gas, in the presence of a bimetallic catalyst based on palladium and platinum as active components;
(b) putting the alcoholic or hydro-alcoholic solution of hydrogen peroxide obtained in step (a) in contact with an olefin and a buffering agent, in the presence of an epoxidation catalyst suspended in the reaction solvent, in order to obtain a reaction mixture containing the epoxide corresponding to the olefin, water and the alcoholic solvent;
(c) treating the alcoholic stream leaving step (b), after separation of the epoxide, in order to eliminate the nitrogenated compounds present;
(d) feeding the alcoholic solvent obtained in (c) to step (a).

The process may comprise a further step (e), wherein the raw hydro-alcoholic mixture of the flash column bottom, is used, when necessary, for diluting the hydro-alcoholic solution of hydrogen peroxide obtained in step (a) to the value required by the epoxidation plant. This advantageously allows a reduction in the volume of solvent to be distilled in the epoxidation reaction plant.

The process for the preparation of epoxides according to the present invention can be described in detail as follows.

In the first step, the process for the synthesis of epoxides comprises:

(a) feeding to a reactor, containing a catalyst based on palladium and platinum, heterogeneous and kept in dispersion in a liquid reaction medium:
(i) a liquid stream consisting of an alcohol or an alcohol-water mixture with a prevalent alcoholic content, containing an acid promoter and a halogenated promoter.
(ii) a gaseous stream containing hydrogen, oxygen and an inert gas, characterized in that the concentration of hydrogen is lower than 4.5% by volume and the concentration of oxygen is lower than 21% by volume, the complement to 100 being an inert gas;
(b) removing from the reactor:
(iii) a liquid stream essentially consisting of the stream (i) and also containing the hydrogen peroxide and water produced by the reaction, characterized in that the concentration of hydrogen peroxide is higher than 3% by weight; and
(iv) a gaseous stream essentially consisting of non-reacted hydrogen and oxygen and the inert gas.

The reactor used can be any reactor suitable for operating in continuous and conducting the reaction in a triphasic system such as that described, obtaining an effective contact between the gaseous phase, liquid phase and catalyst kept in dispersion (so-called slurry system). For example, stirred reactors, bubble reactors, gas-lift reactors with internal or external circulation, such as those described in the state of the art, are suitable for the purpose.

The reactor is maintained under appropriate temperature and pressure conditions. According to the process, object of the invention, the temperature normally ranges from $-10°$ C. to $60°$ C., preferably from $0°$ C. to $40°$ C. The pressure normally ranges from 1 to 300 bars, preferably from 40 to 150 bars.

The residence time of the liquid medium in the reactor normally ranges from 0.05 to 5 hours, preferably from 0.10 to 2 hours.

The catalyst which can be used for the purposes of the invention is a heterogeneous catalyst containing palladium and platinum as active components.

In these catalysts, the palladium is normally present in a quantity ranging from 0.1 to 3% by weight and the platinum in a quantity ranging from 0.01 to 1% by weight, with an atomic ratio between platinum and palladium ranging from 1/500 to 100/100.

The palladium is preferably present in a quantity ranging from 0.4 to 2% by weight and the platinum in a quantity ranging from 0.02 to 0.5% by weight, with an atomic ratio between platinum and palladium ranging from 1/200 to 20/100.

In addition to palladium and platinum, other metals of group VIII or IB, such as, for example, ruthenium, rhodium, iridium and gold, can be present as active components or promoters, in a concentration generally not higher than that of the palladium.

The catalyst can be prepared by dispersing the active components on an inert carrier by means of precipitation and/or impregnation starting from precursors consisting, for example, of solutions of their salts or soluble complexes, and therein reduced to the metal state by means of thermal and/or chemical treatment with reducing substances such as hydrogen, sodium formiate, sodium citrate by means of preparative techniques well known in the state of the art.

The inert carrier may typically consist of silica, alumina, silica-alumina, zeolites, activated carbon, and other materials well known in the state of the art. Activated carbon is preferred for the preparation of the catalysts useful for the invention.

Activated carbons which can be used for the invention are selected from those of fossil or natural origin deriving for example from wood, lignite, peat or coconut and having a surface area higher than 300 m$^2$/g and which can reach 1400 m$^2$/g, in particular those having a surface area higher than 600 m$^2$/g.

Preferred activated carbons are those with a low ash content.

The sulfonated activated carbons described in Italian patent application MI 98A01843 can be used for the purpose.

Before the supporting or impregnation of the metals, the activated carbon can be subjected to treatment such as washing with distilled water or treatment with acids, bases or diluted oxidizing agents, for example acetic acid, hydrochloric acid, sodium carbonate and hydrogen peroxide.

The catalyst is normally suspended in the reaction medium at a concentration ranging from 0.1 to 10% by weight, preferably from 0.3 to 3% by weight.

The liquid stream (i) consists of an alcohol or a mixture of $C_1$–$C_4$ alcohols or a mixture of said alcohols with water with a prevalent alcoholic content. A mixture with a prevalent alcoholic content refers to a mixture containing over 50% by weight of alcohol or mixture of alcohols. Among $C_1$–$C_4$ alcohols, methanol is preferred for the purposes of the invention. Among preferred mixtures is a mixture of methanol and water containing at least 70% by weight of methanol.

The liquid stream also contains an acid promoter and a halogenated promoter.

The acid promoter can be any substance capable of generating H$^+$ hydrogen ions in the reaction liquid medium and is generally selected from inorganic acids such as sulfuric, phosphoric, nitric acid or from organic acids such as sulfonic acids.

Sulfuric acid and phosphoric acid are preferred. The concentration of the acid generally ranges from 0 to 1000 mg per kg of liquid medium and preferably from 10 to 500 mg per kg of liquid medium.

The halogenated promoter can be any substance capable of generating halide ions in the reaction liquid medium. Substances capable of generating bromide ions are preferred. These substances are generally selected from hydrobromic acid and its salts soluble in the reaction medium, for example alkaline bromides, hydrobromic acid being preferred.

The concentration of halogenated promoter generally ranges from 0.1 to 50 mg per kg of liquid medium and preferably from 1 to 10 mg per kg of liquid medium.

The gaseous stream (ii) at the inlet contains a concentration of hydrogen of less than 4.5% by volume and a concentration of oxygen of less than 21% by volume, the complement to 100 being an inert gas, which is generally selected from nitrogen, helium, argon. Said gas is preferably nitrogen.

In the gaseous stream (ii) the concentration of hydrogen preferably ranges from 2% to 4% by volume and the concentration of oxygen preferably ranges from 6% to 18% by volume.

The oxygen can be supplied to said stream using pure or substantially pure oxygen, or enriched air, as raw material, containing for example from 21 to 90% of oxygen or air, the composition of the stream then being brought to the desired values, defined above, by the addition of a suitable concentration of inert gas.

The liquid stream (iii) leaving the reactor normally has a concentration of hydrogen peroxide of over 3% by weight and, preferably from 4% to 10% by weight. It also contains the acid promoter and halogenated promoter in quantities equal to those charged with the liquid stream fed and water in a quantity equal to that charged with the liquid stream fed together with the water obtained as reaction by-product. The latter usually represents an additional concentration of 0.5% to 2.5% by weight.

The liquid stream (iii) is separated from the catalyst by means of filtration techniques well known in the state of the art, for example by the use of filters situated inside the reactor or in a special recirculation cycle of the reaction mixture outside the reactor. In the latter case, the tangential filtration technique can also be conveniently adopted.

The liquid stream (iii) proves to be stable to storage without requiring the addition of stabilizing substances.

The gaseous stream (iv) leaving the reactor, essentially consisting of non-reacted hydrogen and oxygen and the inert gas, generally contains a volume concentration of hydrogen equal to or lower than 2%, normally ranging from 0.5 to 1.5%, and a volume concentration of oxygen generally less than 18%, normally ranging from 6 to 12%.

In an embodiment of the process of the present invention, the gaseous stream leaving the reactor is recycled to the feeding to the reactor, after flushing from the system the fraction necessary for eliminating the quantity of inert gas charged in excess with the feeding, particularly when air is used as oxygen source. In this case, the gaseous stream (ii) fed to the reactor consists of the recycled fraction of the above stream (iv), containing a quantity of hydrogen and oxygen (as such or in the form of air or enriched air) essentially equal to that used up by the reaction and that used for the flushing.

According to another embodiment of the process of the present invention, the gaseous stream (iv) leaving the reactor is fed to one or more subsequent reactors operating analogously to that described above, after adding each time a quantity of hydrogen and oxygen (as such or in the form of air or enriched air) essentially equal to that used up by the reaction which takes place in the single reactors.

Operating under the conditions described above, it is possible to produce hydrogen peroxide under safety conditions with a reaction productivity normally ranging from 30 to 200 g of $H_2O_2$ (expressed as $H_2O_2$ at 100%) per liter of reaction medium per hour and with a molar selectivity towards the formation of $H_2O_2$, referring to the hydrogen used up, generally higher than 70%.

Furthermore, the possibility of minimizing the concentrations of acid and halogenated promoters present in the reaction liquid medium positively influences the stability of the catalytic system; there are no signs of a substantial loss in the catalytic activity after 1000 hours of reaction in continuous.

The filtered liquid stream (iii) is fed to a reaction unit consisting of one or more reactors containing the epoxidation catalyst suspended in the reaction solvent together with the olefin and a buffering agent.

When the concentration of hydrogen peroxide in the liquid stream (iii) is higher than the values required by the epoxidation process (3.5–4.5%), the liquid stream (iii) is diluted with the raw hydro-alcoholic mixture of the flash column bottom to the value required by the epoxidation plant.

The filtered liquid product leaving the reaction unit is fed to a distillation unit consisting of one or more stripping (flash) columns, one for each reactor of the reaction unit, to obtain a product at the head essentially consisting of olefin oxide and non-reacted olefin and a product at the bottom essentially consisting of solvent, non-reacted hydrogen peroxide, water and reaction by-products. The product at the bottom of the distillation unit is fed, for the quota not recycled to the epoxidation reaction unit, to a decomposition unit R4 consisting of one or more reactors containing a decomposition catalyst having the function of decomposing the residual hydrogen peroxide into $O_2$ and $H_2O$.

The mixture leaving the decomposition unit R4, essentially consisting of solvent, oxygen and water, is fed, together with an inert gas (preferably nitrogen), to a phase separator V4 to obtain, at the head, a gaseous phase containing oxygen, inert gas and traces of solvent and, at the bottom, a liquid phase consisting of solvent, water and reaction by-products.

The gaseous phase leaving V4 is fed to a condensation system consisting of one or more condensers in series for the recovery of the residual solvent, whereas the non-condensable compounds (oxygen and inert gas with traces of solvent) are discharged.

The solvent leaving the condensation system and the liquid phase leaving R4 are fed to the distillation column C6-A together with a diluted aqueous or hydro-alcoholic solution containing sulfuric acid (about 10–50 mg/kg of sulfuric acid with respect to the total stream) to obtain, at the head, the purified solvent containing traces of light products and a product, at the bottom, essentially consisting of reaction water and that charged with the hydrogen peroxide, reaction by-products and traces of solvent, which is discharged.

The solvent leaving the condensation system and the liquid phase leaving V4 are preferably fed towards the bottom of the distillation column C6-A, whereas the acid solution is fed at a height equal to about ⅔ of the column. The function of this acid treatment is to completely separate the nitrogenated basic products present in the stream, which could influence the performance of the catalyst used for the synthesis of hydrogen peroxide. The solvent leaving the head of the column C6-A is fed to a column C6-B, in order to separate the light products at the head, whereas the purified solvent is separated at the bottom.

The stream at the head of the column C6-B is sent to a distillation column C6-C, to recover, at the bottom, the solvent without light products, recycled to the hydrogen peroxide synthesis reaction, and a concentrated stream of light products, at the head.

The acid treatment in the column described above, can be substituted by means of treatment on the methanol at the head of C6-A with activated carbon, sulfonic resins or sulfonated carbons (Italian Patent Application MI 98A01843).

The product at the head of the stripping column(s) and the vent products of the reactors are fed to a distillation column C4 to obtain a product, at the head, consisting of non-reacted olefin, recycled to the reaction unit, and a product, at the bottom essentially consisting of olefin oxide.

The product at the bottom of the distillation column is fed to a purification system C5. The residual olefin obtained at the head. C5 is recycled to the reaction unit, the liquid phase, at the bottom, essentially consisting of solvent is recycled to the flash column(s), and the olefin oxide with a commercial purity is obtained from a lateral cut in the upper part of the column.

Olefins which can be used in the process of the present invention are those having general formula (I)

wherein: $R_1$, $R_2$, $R_3$ and $R_4$, the same or different, can be hydrogen, an alkyl radical with from 1 to 20 carbon atoms, an aryl radical, alkylaryl radical with from 7 to 20 carbon atoms, a cyclo-alkyl radical with from 6 to 10 carbon atoms, an alkylcyclo-alkyl radical with from 7 to 20 carbon atoms.

The radicals $R_1$, $R_2$, $R_3$ and $R_4$, can form, in pairs, saturated or unsaturated rings. Furthermore, said radicals can contain halogen atoms, nitro, nitrile, sulfonic and relative ester groups, carbonyl, hydroxyl, carboxyl, thiol, amine and ether groups.

The olefins can carry the above substituents both on unsaturated carbon atoms and in different positions.

Non-limiting examples of olefins having formula (I) are: ethylene, propylene, allyl chloride, allyl alcohol, butenes, pentenes, hexenes, heptenes, octene-1, 1-tridecene, mesityl oxide, isoprene, cyclo-octene, cyclo-hexene or bicyclic compounds such as norbornenes, pinenes, etc.

The preferred olefin is propylene. Propylene with a purity of over 70% is generally used. The propylene is preferably available as a stream from steam cracking with a minimum purity of 96%, the remaining percentage consisting of propane and typical $C_3$ impurities.

The quantity of hydrogen peroxide with respect to the olefin is not critical, but a molar ratio olefin/$H_2O_2$ ranging from 10:1 to 1:10, preferably from 6:1 to 1:1, is preferably used.

The epoxidation reaction can be carried out in one or more liquid solvents at epoxidation temperatures, compatible with hydrogen peroxide and capable of dissolving the olefin and olefin oxide produced.

Solvents of a polar nature consisting of an alcohol or mixture of $C_1$–$C_4$ alcohols or a mixture of said alcohols with water with a prevalent alcoholic content, are typically used. A mixture with a prevalent alcoholic content refers to a mixture containing over 50% by weight of alcohol or mixture of alcohols. Among $C_1$–$C_4$ alcohols, methanol is preferred for the. purposes of the invention. Among the mixtures, a mixture of methanol and water containing at least 70% by weight of methanol, is preferred.

The buffering agent is selected from ammonia, ammonium acetate, ammonium formiate or a system consisting of a nitrogenated base and one of its salts with an organic or inorganic acid as described in Italian patent application MI 99A/001658.

The buffering agent is fed in continuous with one of the reagents streams fed to the epoxidation reactor, in such a quantity as to maintain the pH of the reaction mixture, measured under the operating conditions, at a value higher than 5, preferably ranging from 5.5 to 8.

The epoxidation catalyst which can be used in the process of the present invention is selected from those generally known under the name of titanium silicalites.

For example, titanium-silicalites can be used, with an MFI structure, described in the patent U.S. Pat. No. 4,410,501, which also describes their structural characteristics.

Titanium silicalites in which part of the titanium is substituted by other metals such as boron, aluminum, iron or gallium, can also be used. These substituted titanium silicalites and the methods for their preparation are described in European patent applications 226,257, 226,258 and 266,825.

Titanium silicalites with a MEL or intermediate MFI/MEL structure, described in Belgian patent 1,001,038, can also be used. Other titanium-silicalites can be selected from beta zeolites containing titanium and having a BEA structure, described in Spanish patent 2,037,596, ZSM-12 containing titanium and optionally aluminum, described in "Journal of Chemical Communications, 1992, page 745".

The preferred catalyst according to the present invention is titanium-silicalite having general formula (II):

$$x\text{TiO}_2 \cdot (1-x)\text{SiO}_2$$

wherein: x represents a number ranging from 0.0001 to 0.04, preferably the value of x ranges from 0.01 to 0.025, and described, for example in patents U.S. Pat. Nos. 4.410,501, 4,824,976, 4,666,692, 4,656,016, 4,859,785, 4,937,216.

The catalyst can be used in the form of powder, pellets, microspheres, extruded or other convenient physical forms.

The use of a ligand (co.gel) or an inert carrier combined with the catalyst can be advantageous. Supported catalysts can be prepared using known methods.

The inert carrier may typically consist of silica, alumina, silica-alumina, zeolites, activated carbon, and other materials well known in the state of the art.

The quantity of catalyst used in the process of the present invention is not critical; it is selected however so as to allow epoxidation reaction to be completed in the shortest possible time.

The quantity of catalyst is generally selected in relation to the various parameters, such as the reaction temperature, reactivity and concentration of the olefin, the concentration of hydrogen peroxide, type and composition of the solvent, catalytic activity and type of reactor or reaction system used.

The quantity of catalyst typically ranges from 1 to 15% by weight with respect to the reaction mixture, preferably from 4 to 10% by weight. 10 The temperature used in the process of the present invention generally ranges from 20 to 150° C., preferably from 40 to 100° C., from 55 to 90° C. is particularly preferred.

The operating pressure is such as to allow the olefin to be maintained in liquid phase at the temperature pre-selected for the reaction. In general, the operating pressure is higher than atmospheric pressure when gaseous olefins are used.

The reactor used in the epoxidation reaction can be any reactor suitable for operating in continuous and conducting the reaction in a system such as that described, obtaining an effective contact between the olefin, the liquid phase and catalyst kept in suspension.

For example, stirred reactors, bubble reactors, gas-lift reactors with internal or external circulation or CSTR (Continuous Stirred Tank Reactors) or PFR (Plug Flow Reactors), as described in the state of the art, are suitable for the purpose.

The olefin charged, this term referring to fresh olefin, recycled olefin or their mixtures, is fed to the reaction step under flow-rate control and in excess to maximize the conversion and selectivity to olefin oxide and maintain the reaction pressure. A mixture consisting of fresh olefin deriving from battery limits and recycled olefin is preferably fed. Before entering the reaction unit, the fresh olefin can be purified in the distillation column C4.

According to an embodiment of the process of the present invention, the reaction unit is made up of three reactors R1-R2-R3 of the CSTR type and isotherms.

The reactors R1 and R2 operate under substantially identical conditions, i.e. at a temperature of about 55–75° C. and a pressure of 13 bars, whereas the reactor R3, which acts as finishing reactor, i.e. with exhaustion of the hydrogen peroxide fed to the reactors R1 and R2, operates at a temperature of 79–90° C. and a pressure of 8 bars.

The overall oxidation reaction of the olefin is carried out in such a way as to have a concentration of $H_2O_2$ of less than 100 ppm in the stream leaving the unit R3.

In the first and second reactor, the reaction selectivity with respect to hydrogen peroxide is 98% molar with a conversion of 96%, in the third reactor there is a selectivity of 80% molar and a conversion of 95%. The flash columns substantially operate under the same operating conditions and discharge, at the head, streams in vapour phase essentially consisting of non-reacted olefin, olefin oxide, inert products, for example aliphatic hydrocarbons such as propane, and solvent vapours. At the bottom, the columns discharge streams in liquid phase with a differentiated composition, which for C1 and C2 are partly recycled to the respective synthesis reactors R1 and R2.

The vapours at the head of columns C1-C2-C3 are fed to a distillation column C4 to recover the non-reacted olefin at the head. The latter is recycled to the synthesis of the olefin oxide after partial elimination of the inert products. The vapours coming from the vents of reactors R1-R2-R3, are also fed to the column C4.

The temperature at the bottom of the column C4 must not exceed 80° C. with residence times in the order of 1 minute; this is to avoid degradation of the olefin oxide.

Whereas the streams at the bottom of the distillation columns C1 and C2 still contain significant quantities of hydrogen peroxide, and are therefore recycled to the synthesis of the olefin oxide, the stream at the tail of the column C3 is substantially without $H_2O_2$ and essentially consists of solvent, water and reaction by-products.

This stream is fed to a decomposition section of the residual hydrogen peroxide R4 consisting of one or more fixed bed tubular reactors arranged in series.

The hydrogen peroxide decomposition reaction is exothermic and takes place in liquid phase at about 80–90° C., with a residence time ranging from 1 to 10 minutes, preferably from 2 to 5 minutes.

Examples of catalysts used in the decomposition reaction consist of metals of group VIII or their oxides. The carriers are selected from those of the known art and indicated above.

The mixture leaving R4 is fed to a phase separator V4 which separates the oxygen generated from the decomposition of the hydrogen peroxide and the dilution inert product, preferably nitrogen, charged downstream of the reactor R4 to maintain the solvent/oxygen mixture released in the flash column below the lower flammability limit.

The solvent-oxygen-inert product mixture leaving V4, is then condensed in two condensers in series to recover the solvent, whereas the non-condensable products (oxygen and inert product with traces of solvent) are discharged.

The liquid phase leaving R4 and the liquid mixture leaving V4 are fed to the distillation column C6-A and treated as described above.

The condensation heat recovered at the head of the column C6-A can be used to supply all the reboiling units present in the process. In this case, the pressure of the column is kept at a suitable value for this purpose.

A liquid stream rich in olefin oxide is extracted from the bottom of the distillation column C4, and is sent to a purification section C5.

The latter consists of two columns in series due to the high number of plates and separates, at the head, residual vapours still present (non-reacted olefin and inert gases), at the bottom, a liquid stream containing solvent and olefin oxide (recycled to the distillation column C3) and, laterally, a liquid stream consisting of olefin oxide with a commercial purity (>99.8%).

The vapours extracted from the head of the purification column C5 may still contain significant quantities of olefin oxide and are recycled upstream of the distillation column C4.

Operating with the process of the present invention, the epoxidation catalyst, after 1000 hours, does not show any sign of deterioration and the productivity and reaction selectivity are high.

The process for the preparation of olefin oxides can be better understood by referring to the block schemes of FIG. 1, which represents an illustrative but non-limiting embodiment.

Figure 1:
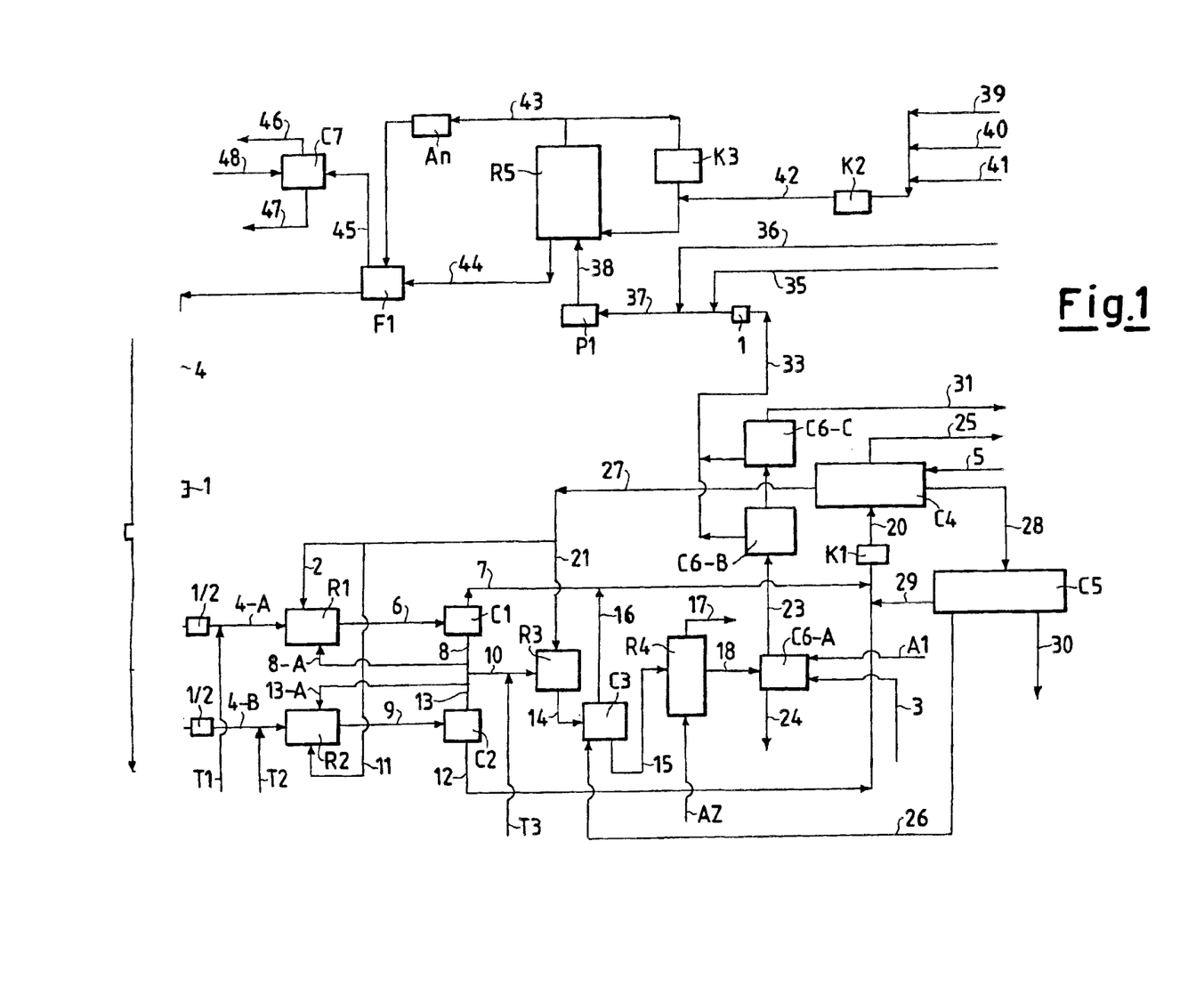

With reference to FIG. 1, the olefin, for example propylene, is fed in parallel to the reactors R1-R2-R3 with lines (2)-(11)-(21). The buffering agent is fed to the reactors R1-R2-R3 parallelly with lines (T1)-(T2)-(T3), whereas half of the recycled solvent with the hydrogen peroxide (4) is fed to the reactor R1 (4A) and the other half to R2 (4B). Possible solvent losses in the integrated production cycle are replaced by means of "make-up" line (3) which enters with the feeding of column C6-A.

Propylene Oxide Synthesis Reaction

The filtered liquid reaction product leaving the first reactor R1 is fed with line (6) to the first distillation column C1 from whose head the propylene oxide produced and non-reacted propylene (7), in vapour phase, are recovered, and from the bottom, a liquid stream (8) still containing hydrogen peroxide, a part of (8) is fed to the reactor R3 and the remaining stream (8A) is recycled to the reactor R1 to dilute the hydrogen peroxide to the desired concentration.

The filtered liquid reaction product leaving the second reactor R2 is fed with line (9) to the second distillation column C2 from whose head the propylene oxide produced and non-reacted propylene (12), in vapour phase, are recovered, and from the bottom, a liquid stream (13) still containing hydrogen peroxide, a part of (13) is fed to the reactor R3 and the remaining stream (13A) is recycled to the reactor R2 to dilute the hydrogen peroxide to the desired concentration.

The filtered liquid reaction product leaving the second reactor R3 is fed with line (14) to the third distillation column C3 from whose head the propylene oxide produced and non-reacted propylene (16), in vapour phase, are recovered, and from the bottom, a liquid stream (15) still containing hydrogen peroxide, fed to the reactor system R4 (the system R4 refers to the reactor R4 itself, a phase separator V4 and two condensers in series E421/E422 on the vapour phase leaving V4).

The liquid reaction product leaving the system R4 is fed to the column C6-A (18), the gaseous product vented into the atmosphere containing oxygen, nitrogen and traces of methanol is represented by line (17). The diluting nitrogen is fed to the system R4 with line (AZ).

Recovery of the Solvent

The liquid product leaving the reactor system R4, without hydrogen peroxide and essentially consisting of solvent, water and by-products, is fed with line (18) to the solvent recovery section consisting in this particular case of a series of distillation columns C6 A-B-C. Water and the reaction by-products (24) are discharged from the bottom of C6-A. At the head of C6-A, the solvent (23) is recovered and sent to the column C6-B. At about ⅔ of the height of C6-A an acid solution (A1) is fed, which blocks the nitrogenated compounds present in vapour phase. The head of the column C6-B consisting of light compounds (methyl formiate, dimethoxymethane) present in the methanol at the inlet of C6-A, at a concentration of 1–2% by weight of methanol, is fed to the column C6-C. The light concentrated products (6–8% by weight) leave the head of the column C6-C with the flushing stream (31). The bottom products of columns C6-B and C6-C when joined (33), form the methanol recycled to the synthesis reaction of hydrogen peroxide.

Recovery of the Propylene Oxide

The streams (7), (12) and (16), together with the vented products of the synthesis reactors, consist of non-reacted propylene, propylene oxide and solvent; they are fed, by means of the compressor K1, to the distillation column C4. The propylene is separated at the head of the column C4 together with the inert products (27)+(25). The inert products, such as propane, are inserted into the cycle together with fresh propylene (5). To prevent there being an accumulation of inert products in the production cycle, a part of the stream of propylene recycled to the reactors, is flushed (25).

A stream rich in propylene oxide (28) is recovered at the bottom of the column C4 and is fed to the purification section of propylene oxide, in this particular case consisting of a distillation column C5 (in two sections). A stream in vapour phase (29) still containing traces of non-reacted propylene and propylene oxide is recovered at the head of the column C5; this stream is recycled by means of the compressor K1 to the column C4. A liquid stream (26) containing propylene oxide and solvent is extracted from the bottom of the column C5 and is sent back to the column C3.

The propylene oxide with a commercial purity is extracted from the column C5 as a lateral cut (30).

Synthesis Reaction of Hydrogen Peroxide

The stream of distilled methanol (33) coming from the propylene oxide synthesis section goes to the hydrogen peroxide synthesis section.

A stream (35) of an aqueous solution of HBr (halogenated promoter) and a stream (36) of an aqueous solution of $H_2SO_4$ (acid promoter) are added to the stream (33); the pump P1 sends the mixture obtained (37) to the hydrogen peroxide synthesis reactor R5 at a pressure of 100 bars. The streams (39)-(40)-(41) of hydrogen, oxygen and nitrogen, respectively, are sent by means of the compressor K2 to the reactor R5 at 100 bars. The ventilator K3 recycles the non-reacted gases from the top of the reactor into the reaction medium. The stream (44), consisting of the reaction products hydrogen peroxide and water, the methanol solvent and reaction gases dissolved at 100 bars, is fed to the flash column F1 at low pressure. The vapour phase leaving F1, after condensation (45), feeds the separation column C7 fed at the head with water (48). The gases at the head C7 (46) are flushed from the cycle, the stream (47) at the bottom of the column C7 containing traces of methanol and water is sent to a biological treatment system. The gases of the top of the reactor removed for analysis with the on-line analyzer An, are also sent to the flash column F1.

The liquid stream (4) leaving F1 consists of hydrogen peroxide (7% weight), water and methanol. Said stream forms the feeding stream to the propylene oxide synthesis Compared with the known methods, the process described above allows epoxides to be obtained with a high productivity over a period of time and a high selectivity, using a method which can be easily applied on an industrial scale and with the possibility of operating in continuous.

The following operative example is provided for illustrative purposes and does not limit the scope of the invention.

EXAMPLE 1

The procedure is adopted according to FIG. 1 to produce propylene oxide starting from:

- a stream deriving from a steam cracking plant consisting of 99.5% by weight of propylene and 0.05% by weight of propane;
- a gaseous stream containing hydrogen, oxygen and nitrogen, characterized in that the concentration of hydrogen is lower than 4.5% by volume and the concentration of oxygen is lower than 21% by volume, the complement to 100 being nitrogen;
- make-up methanol;
- an acid promoter $H_2SO_4$ (200 mg per kg of liquid medium) and a halogenated promoter HBr (6 mg per kg of liquid medium) fed to the methanol stream at the inlet of R5;
- a buffering agent consisting of an aqueous solution of $NH_4OH$, fed to the stream of methanol at the inlet of reactors R1-R2-R3 in such a quantity as to buffer the pH of the reaction mixture to a value of 6.5 (present in the liquid stream in the feeding to R1-R2-R3 in a concentration of 80 ppm); a reinforced glass pH-meter inserted in the reaction stream, is used;
- a diluted solution containing sulfuric acid (about 10–50 mg/kg of sulfuric acid with respect to the total stream (18), fed to the column C6-A to obtain a distillation under acid conditions of the methanol recycled to R5.

The titanium silicalite catalyst, of the type described in patent U.S. Pat. No. 4,937,216, is present in the reactors R1, R2 and R3 in a concentration of 6% by weight with respect to the slurry.

The catalyst bed of the decomposer R4, in pellets with an active phase of 15%, is charged in volume excess to guarantee exhaustion of the hydrogen peroxide.

The heterogeneous catalyst based on palladium and platinum is kept in dispersion in the liquid reaction medium at 1% by weight in R5.

Table 1 enclosed (3 pages) indicates the balances and composition of the single streams.

TABLE 1-A

| | Streams | | | | | | | |
|---|---|---|---|---|---|---|---|---|
| | 2 | | 3 | | 4 | | 4A | |
| Components | (kg/h) | (%) | (kg/h) | (%) | (kg/h) | (%) | (kg/h) | (%) |
| Propylene | 411.63 | 93.95 | | | | | | |
| Propane | 26.50 | 6.05 | | | | | | |
| Propylene oxide (PO) | | | | | | | | |
| Methanol (MeOH) | 0.00 | 0.01 | 7.70 | 100 | 2069.10 | 89.68 | 1034.55 | 89.68 |
| Water (H2O) | 0.00 | 0.00 | | | 78.22 | 3.39 | 39.11 | 3.39 |
| Hydrogen peroxide (H2O2) | 0.00 | 0.00 | 0.00 | 0.00 | 160.00 | 6.93 | 80.00 | 6.93 |
| Methoxypropanol | 0.00 | 0.00 | 0.00 | 0.00 | 0.00 | 0.00 | 0.00 | 0.00 |
| 1,2propandiol | 0.00 | 0.00 | 0.00 | 0.00 | 0.00 | 0.00 | 0.00 | 0.00 |
| FLOW RATE | 438.1 | 100 | 7.70 | 100 | 2307.3 | 100 | 1153.7 | 100 |
| Temperature | −14.50 | | 35.00 | | 35.00 | | 35.00 | |
| Pressure | 16.00 | | 16.00 | | 16.00 | | 16.00 | |

| | Streams | | | | | | | |
|---|---|---|---|---|---|---|---|---|
| | 4B | | 5 | | 6 | | 7 | |
| Components | (kg/h) | (%) | (kg/h) | (%) | (kg/h) | (%) | (kg/h) | (%) |
| Propylene | | | 207.3 | 99.50 | 318.2 | 11.92 | 318.2 | 60.25 |
| Propane | | | 1.035 | 0.50 | 26.5 | 0.99 | 26.5 | 5.03 |
| Propylene oxide (PO) | | | | | 128.4 | 4.81 | 128.4 | 24.31 |
| Methanol (MeOH) | 1034.55 | 89.68 | | | 2067.9 | 77.44 | 55.0 | 10.41 |
| Water (H2O) | 39.11 | 3.39 | | | 118.7 | 4.45 | 0.0 | 0.00 |
| Hydrogen peroxide (H2O2) | 80.00 | 6.93 | | | 4.8 | 0.18 | 0.0 | 0.00 |
| Methoxypropanol | 0.00 | 0.00 | | | 4.9 | 0.18 | 0.0 | 0.00 |
| 1,2propandiol | 0.00 | 0.00 | | | 1.0 | 0.04 | 0.0 | 0.00 |
| FLOW RATE | 1153.7 | 100 | 208.3 | 100 | 2670.5 | 100 | 528.2 | 100 |
| Temperature | 35.00 | | 37.50 | | 50.00 | | 36.60 | |
| Pressure | 16.00 | | 16.00 | | 13.00 | | 1.80 | |

| | Streams | | | | | | | |
|---|---|---|---|---|---|---|---|---|
| | 17 | | 18 | | 8-A | | 13-A | |
| Components | (kg/h) | (%) | (kg/h) | (%) | (kg/h) | (%) | (kg/h) | (%) |
| Propylene | | | | | | | | |
| Propane | | | | | | | | |
| Propylene oxide (PO) | 0.0 | 0.00 | 0.0 | 0.00 | | | | |
| Methanol (MeOH) | 0.6 | 27.46 | 2065.2 | 92.25 | 1034.5 | 96.04 | 1034.54 | 96.04 |
| Water (H2O) | 0.003 | 0.13 | 162.5 | 7.26 | 39.11 | 3.63 | 39.11 | 3.63 |
| Hydrogen peroxide (H2O2) | | | 0.0 | 0.00 | 1.6 | 0.15 | 1.60 | 0.15 |
| Methoxypropanol | | | 9.08 | 0.41 | 1.6 | 0.15 | 1.63 | 0.15 |
| 1,2propandiol | | | 1.92 | 0.09 | 0.343 | 0.03 | 0.34 | 0.03 |

TABLE 1-A-continued

| | | | | | | | | |
|---|---|---|---|---|---|---|---|---|
| Oxygen | 0.15 | 6.61 | | | | | | |
| NH4OH | | | | | | | | |
| H2SO4 | | | | | | | | |
| Nitrogen | 1.5 | 65.80 | 0.000 | 0.00 | | | | |
| FLOW RATE | 2.3 | 100 | 2238.7 | 100 | 1077.2 | 100 | 1077.2 | 100 |
| Temperature | −15.00 | | 67.30 | | 84.30 | | 40.00 | |
| Pressure | 1.10 | | 1.20 | | 16.00 | | 16.00 | |

| | Streams | | | | | | | |
|---|---|---|---|---|---|---|---|---|
| | 21 | | 22 | | 23 | | 24 | |
| Components | (kg/h) | (%) | (kg/h) | (%) | (kg/h) | (%) | (kg/h) | (%) |
| Propylene | 202.6 | 93.95 | 0.00 | 0.00 | | | | |
| Propane | 13.0 | 6.05 | 0.00 | 0.00 | | | | |
| Propylene oxide (PO) | | | 0.001 | 0.00 | 0.00 | 0.00 | | |
| Methanol (MeOH) | | | 2065.87 | 92.25 | 2072.9 | 97.04 | 0.0 | 0.00 |
| Water(H2O) | | | 162.49 | 7.26 | 63.28 | 2.96 | 99.2 | 90.02 |
| Hydrogen peroxide (H2O2) | | | 0.00 | 0.00 | | | | |
| Methoxypropanol | | | 9.08 | 0.41 | 0.00 | 0.00 | 9.08 | 8.24 |
| 1,2propandiol | | | 1.92 | 0.09 | | | 1.92 | 1.74 |
| Oxygen | | | 0.15 | 0.007 | | | | |
| NH4OH | | | | | | | | |
| H2SO4 | | | | | | | | |
| Nitrogen | | | | | 0.02 | 0.00 | | |
| FLOW RATE | 215.6 | 100 | 2239.5 | 100 | 2136.2 | 100 | 110.2 | 100 |
| Temperature | −1450 | | 89.8 | | 87.00 | | 128.60 | |
| Pressure | 16.00 | | 10 | | 2.50 | | 2.66 | |

TABLE 1-B

| | Streams | | | | | | | | | |
|---|---|---|---|---|---|---|---|---|---|---|
| | 8 | | 9 | | 10 | | 11 | | 12 | |
| Components | (kg/h) | (%) | (kg/h) | (%) | (kg/h) | (%) | (kg/h) | (%) | (kg/h) | (%) |
| Propylene | 0.0 | 0.00 | 318.2 | 11.92 | 0.0 | 0.00 | 411.63 | 93.95 | 318.2 | 60.25 |
| Propane | 0.0 | 0.00 | 26.5 | 0.99 | 0.0 | 0.00 | 26.50 | 6.05 | 26.5 | 5.03 |
| Propylene oxide (PO) | 0.000 | 0.00 | 128.4 | 4.81 | 0.0 | 0.00 | | | 128.4 | 24.31 |
| Methanol (MeOH) | 2012.9 | 93.96 | 2067.9 | 77.44 | 1956.8 | 91.86 | | | 55.0 | 10.41 |
| Water (H2O) | 118.7 | 5.54 | 118.7 | 4.45 | 159.2 | 7.47 | | | 0.0 | 0.00 |
| Hydrogen peroxide (H2O2) | 4.8 | 0.22 | 4.8 | 0.18 | 6.4 | 0.30 | | | 0.0 | 0.00 |
| Methoxypropanol | 4.9 | 0.23 | 4.9 | 0.18 | 6.5 | 0.31 | | | 0.0 | 0.00 |
| 1,2propandiol | 1.0 | 0.05 | 1.0 | 0.04 | 1.4 | 0.06 | | | 0.0 | 0.00 |
| FLOW RATE | 2142.4 | 100 | 2670.5 | 100 | 2130.3 | 100 | 438.1 | 100 | 528.2 | 100 |
| Temperature | 84.30 | | 50.00 | | 30.00 | | −14.50 | | 50.00 | |
| Pressure | 1.94 | | 13.00 | | 16.00 | | 16.00 | | 16.00 | |

| | Streams | | | | | | | |
|---|---|---|---|---|---|---|---|---|
| | 13 | | 14 | | 15 | | 16 | |
| Components | (kg/h) | (%) | (kg/h) | (%) | (kg/h) | (%) | (kg/h) | (%) |
| Propylene | 0.0 | 0.00 | 195.2 | 8.32 | 0.0 | 0.00 | 196.2 | 55.70 |
| Propane | 0.0 | 0.00 | 12.9 | 0.55 | 0.000 | 0.00 | 12.9 | 3.68 |
| Propylene oxide (PO) | 0.0 | 0.00 | 8.30 | 0.35 | | | 51.6 | 14.71 |
| Methanol (MeOH) | 2012.9 | 93.96 | 1955.9 | 83.37 | 2065.87 | 92.25 | 90.0 | 25.68 |
| Water (H2O) | 118.7 | 5.54 | 162.3 | 6.92 | 162.32 | 7.25 | 0.76 | 0.22 |
| Hydrogen peroxide (H2O2) | 4.8 | 0.22 | 0.3 | 0.01 | 0.3 | 0.01 | 0.0 | 0.00 |
| Methoxypropanol | 4.9 | 0.23 | 9.1 | 0.39 | 9.1 | 0.41 | 0.0 | 0.00 |
| 1,2propandiol | 1.0 | 0.05 | 1.9 | 0.08 | 1.9 | 0.09 | 0.0 | 0.00 |
| FLOW RATE | 2142.4 | 100 | 2345.9 | 100 | 2239.5 | 100 | 350.4 | 100 |
| Temperature | 50.00 | | 37.80 | | 88.20 | | 40.00 | |
| Pressure | 13.00 | | 1.80 | | 2.01 | | 1.10 | |

| | Streams | | | | | | | | | |
|---|---|---|---|---|---|---|---|---|---|---|
| | 25 | | 26 | | 27 | | 28 | | 29 | |
| Components | (kg/h) | (%) | (kg/h) | (%) | (kg/h) | (%) | (kg/h) | (%) | (kg/h) | (%) |
| Propylene | 10.000 | 90.62 | | | 1028.8342 | 93.98 | 3.00 | 2.01 | 2.9910 | 2.72 |
| Propane | 1.035 | 9.38 | | | 65.9410 | 6.02 | 0.29 | 0.19 | 0.2850 | 0.26 |

TABLE 1-B-continued

| | | | | | | | | | | |
|---|---|---|---|---|---|---|---|---|---|---|
| Propylene oxide (PO) | | | 43.3 | 17.72 | | 0.00 | 0.00 | 106.7210 | 97.02 |
| Methanol (MeOH) | | | 200.0 | 81.96 | | 145.00 | 97.28 | 0.0020 | 0.00 |
| Water (H2O) | | | 0.77 | 0.32 | | 0.77 | 0.51 | 0.0010 | 0.00 |
| Hydrogen peroxide (H2O2) | | | | | | 0.00 | 0.00 | | |
| Methoxypropanol | | | | | | 0.00 | 0.00 | | |
| 1,2propandiol | | | | | | | | | |
| Oxygen | | | | | | | | | |
| NH4OH | | | | | | | | | |
| H2SO4 | | | | | | | | | |
| Nitrogen | | | | | | | | 0.0000 | 0.00 |
| FLOW RATE | 11.0 | 100 | 244.0 | 100 | 1094.8 | 100 | 149.1 | 100 | 110.0 | 100 |
| Temperature | −14.30 | | 63.40 | | −14.50 | | 75.30 | | 37.60 | |
| Pressure | 3.80 | | 1.68 | | 3.80 | | 3.88 | | 1.20 | |

| | Streams | | | | | | | | | |
|---|---|---|---|---|---|---|---|---|---|---|
| | 30 | | T 1-2-3 | A1 | AZ | | 33 | |
| Components | (kg/h) | (%) | (%) | (%) | (kg/h) | (%) | (kg/h) | (%) |
| Propylene | 0.0090 | | | | | | | |
| Propane | 0.0010 | | | | | | | |
| Propylene oxide (PO) | 265.114 | 99.99 | | | | | | |
| Methanol (MeOH) | 0.0120 | | | | | | 2068.9 | 97.03 |
| Water (H2O) | 0.0020 | | 90.00 | 90.00 | | | 63.28 | 2.97 |
| Hydrogen peroxide (H2O2) | | | | | | | | |
| Methoxypropanol | | | | | | | | |
| 1,2propandiol | | | | | | | | |
| Oxygen | | | | | | | | |
| NH4OH | | | 10.00 | | | | | |
| H2SO4 | | | | 10.00 | | | | |
| Nitrogen | | | | | 1.50 | 100.0 | | |
| FLOW RATE | 265.1 | 100 | 100 | 100 | 1.5 | 100 | 2132.2 | 100 |
| Temperature | 39.10 | | 30.00 | 30.00 | 30.00 | | | |
| Pressure | 1.22 | | 16.00 | 16.00 | 16.00 | | | |

TABLE 1-C

| | Streams | | | | | | | | | | | | | |
|---|---|---|---|---|---|---|---|---|---|---|---|---|---|---|
| | 31 | | 35 | | 36 | | 37 | | 38 | | 40 | | 41 | |
| Components | (kg/h) | (%) | (kg/h) | (%) | (kg/h) | (%) | (kg/h) | (%) | (kg/h) | (%) | (kg/h) | (%) | (kg/h) | (%) |
| Hydrogen | | | | | | | | | | | | | | |
| Oxygen | | | | | | | | | | | 182.9 | 100 | | |
| Nitrogen | | | | | | | | | | | | | 43.9 | 100.00 |
| Methanol (MeOH) | 4.00 | 100.00 | | | | | 2068.94 | 96.88 | | 99.84 | | | | |
| Water (H2O) | | | 0.26 | 96.30 | 2.61 | 85.02 | 66.15 | 3.10 | | 0.14 | | | | |
| Hydrogen peroxide (H2O2) | | | | | | | | | 0.00 | 0.00 | | | | |
| HBr | | | 0.01 | 3.70 | | | 0.01 | 0.00 | 0.0 | 0.00 | | | | |
| H2SO4 | | | | | 0.46 | 14.98 | 0.46 | 0.02 | 0.5 | 0.02 | | | | |
| FLOW RATE | 4.0 | 100 | 0.27 | 100 | 3.1 | 100 | 2135.6 | 100 | 0.5 | 100 | 182.9 | 100 | 43.9 | 100 |
| Temperature | 35.00 | | 35.00 | | 35.00 | | 35.00 | | 35.00 | | −180.00 | | 30.00 | |
| Pressure | 2.50 | | 2.50 | | 2.50 | | 2.50 | | 100.00 | | 4.00 | | 3.10 | |

| | Streams | | | | | | | | | | | | | |
|---|---|---|---|---|---|---|---|---|---|---|---|---|---|---|
| | 42 | | 43 | | 44 | | 45 | | 46 | | 48 | | 47 | |
| Components | (kg/h) | (%) | (kg/h) | (%) | (kg/h) | (%) | (kg/h) | (%) | (kg/h) | (%) | (kg/h) | (%) | (kg/h) | (%) |
| Hydrogen | 12.6 | 5.25 | 0.00 | 1.30 | 0.0 | 0.00 | 0.0 | 0.06 | 0.0 | 0.06 | | | | |
| Oxygen | 182.9 | 76.41 | 0.00 | 6.10 | 7.2 | 0.31 | 7.2 | 14.13 | 7.2 | 14.15 | | | | |
| Nitrogen | 43.9 | 18.34 | 0.00 | 92.60 | 43.9 | 1.86 | 43.9 | 85.71 | 43.9 | 85.80 | | | | |
| Methanol (MeOH) | | | | | 2069.1 | 87.71 | 0.05 | 0.10 | | | | | 0.1 | 0.05 |
| Water (H2O) | | | | | 78.2 | 3.32 | | | | | 100.00 | 100.00 | 100.0 | 99.95 |
| Hydrogen peroxide (H2O2) | | | | | 160.0 | 6.78 | | | | | | | | |
| HBr | | | | | 0.01 | 0.00 | | | | | | | | |
| H2SO4 | | | | | 0.46 | 0.02 | | | | | | | | |

TABLE 1-C-continued

| FLOW RATE | 239.4 | 100 | 0.0 | 100 | 2359.0 | 100 | 51.2 | 100 | 51.2 | 100 | 100.0 | 100.0 | 100.1 | 100 |
|---|---|---|---|---|---|---|---|---|---|---|---|---|---|---|
| Temperature | 30.00 | | 30.00 | | 30.00 | | 30.00 | | 30.00 | | 30.00 | | 30.00 | |
| Pressure | 100.00 | | 100.00 | | 100.00 | | 1.50 | | 1.00 | | 1.00 | | 1.00 | |

What is claimed is:

1. An integrated process for the continuous production of epoxides by the direct oxidation of an olefin with hydrogen peroxide which comprises:
   (a) preparing an alcoholic or hydro-alcoholic solution of hydrogen peroxide in a concentration of over 3% by weight, using a gaseous stream containing hydrogen, oxygen and an inert gas, in the presence of a bimetallic catalyst based on palladium and platinum as active components;
   (b) putting the alcoholic or hydro-alcoholic solution of hydrogen peroxide obtained in step (a) in contact with an olefin and a buffering agent, in the presence of an epoxidation catalyst suspended in the reaction solvent, in order to obtain a reaction mixture containing the epoxide corresponding to the olefin, water and the alcoholic solvent;
   (c) treating the alcoholic stream leaving step (b), after separation of the epoxide, in order to eliminate the nitrogenated compounds present;
   (d) feeding the alcoholic solvent obtained in (c) to step (a).

2. The process according to claim 1, wherein in step (c) the treatment of the alcoholic stream is effected by distilling the solvent together with an aqueous or diluted hydro-alcoholic solution containing sulfuric acid in a quantity of about 10–50 mg/kg of sulfuric acid with respect to the total stream, or by treating the distilled solvent with activated carbons, sulfonic resins or sulfonated carbons.

3. The process according to claim 1, which comprises a further step (e), wherein the raw hydro-alcoholic mixture of the flash column bottom is used for diluting the alcoholic or hydro-alcoholic solution of hydrogen peroxide leaving step (a) to the value required by the epoxidation plant.

4. The process according to claim 1, wherein step (a) for the production in continuous of alcoholic or hydro-alcoholic solutions of hydrogen peroxide comprises:
   (a') feeding to a reactor, containing a catalyst based on palladium and platinum, heterogeneous and kept in dispersion in a liquid reaction medium:
   (i) a liquid stream consisting of an alcohol or an alcohol-water mixture with a prevalent alcoholic content, containing an acid promoter and a halogenated promoter:
   (ii) a gaseous stream containing hydrogen, oxygen and an inert gas, characterized in that the concentration of hydrogen is lower than 4.5% by volume and the concentration of oxygen is lower than 21% by volume, the complement to 100 being an inert gas;
   (b') removing from the reactor:
   (iii) a liquid stream essentially consisting of the stream (i) and also containing the hydrogen peroxide and water produced by the reaction, characterized in that the concentration of hydrogen peroxide is higher than 3% by weight; and
   (iv) a gaseous stream essentially consisting of non-reacted hydrogen and oxygen and the inert gas.

5. The process according to claim 1, wherein the catalyst in step (a') contains palladium in a quantity ranging from 0.1 to 3% by weight and platinum in a quantity ranging from 0.01 to 1% by weight, with an atomic ratio platinum and palladium ranging from 1/500 to 100/100.

6. The process according to claim 5, wherein the catalyst contains a quantity of palladium ranging from 0.4 to 2% by weight and a quantity of platinum ranging from 0.02 to 0.5% by weight, with an atomic ratio platinum and palladium ranging from 1/200 to 20/100.

7. The process according to claim 5, wherein the catalyst, in addition to palladium and platinum, contains another metal selected from those of group VIII or IB.

8. The process according to claim 7, wherein the metal is ruthenium, rhodium, iridium or gold.

9. The process according to claim 4, wherein the catalyst is prepared by dispersing the active components on an inert carrier by means of precipitation and/or impregnation.

10. The process according to claim 9, wherein the inert carrier is selected from silica, alumina, silica-alumina, zeolites, activated carbon and activated carbon functionalized with sulfonic groups.

11. The process according to claim 10, wherein the carrier is an activated carbon selected from those of fossil or natural origin deriving from wood, lignite, peat or coconut and having a surface area higher than 300 m$^2$/g.

12. The process according to claim 11, wherein the carrier is an activated carbon having a surface area which can reach a value of 1400 m$^2$/g.

13. The process according to claim 12, wherein the carrier is an activated carbon with a surface area higher than 600 m$^2$/g.

14. The process according to claim 11, wherein the activated carbon has a low ash content.

15. The process according to claim 4, wherein the catalyst is dispersed in the reaction medium at a concentration ranging from 0.1 to 10% by weight.

16. The process according to claim 15, wherein the catalyst is dispersed in the reaction medium at a concentration ranging from 0.3 to 3% by weight.

17. The process according to claim 4, wherein the liquid stream (i) consists of an alcohol or mixture of $C_1$–$C_4$ alcohols or a mixture of said alcohols with water with an alcoholic content higher than 50%.

18. The process according to claim 17, wherein the alcohol is methanol.

19. The process according to claim 17, wherein the mixture is a mixture of methanol and water containing at least 70% by weight of methanol.

20. The process according to claim 4, wherein the halogenated promoter is a substance capable of generating halogen ions in the liquid reaction medium.

21. The process according to claim 20, wherein the halogenated promoter is selected from substances capable of generating bromide ions such as hydrobromic acid and its salts soluble in the reaction medium, such as alkaline bromides.

22. The process according to claim 21, wherein the promoter is hydrobromic acid.

23. The process according to claim 4, wherein the concentration of the halogenated promoter ranges from 0.1 to 50 mg per kg of solution.

24. The process according to claim 23, wherein the concentration of the halogenated promoter ranges from 1 to 10 mg per kg of solution.

25. The process according to claim 4, wherein the acid promoter is selected from substances capable of generating $H^+$ hydrogen ions in the reaction medium.

26. The process according to claim 25, wherein the acid promoter is selected from inorganic acids such as sulfuric, phosphoric, nitric acid or organic acids such as sulfonic acids.

27. The process according to claim 26, wherein the acid promoter is sulfuric acid or phosphoric acid.

28. The process according to claim 4, wherein the concentration of acid promoter ranges from 0 to 1000 mg per kg of solution.

29. The process according to claim 28, wherein the concentration of acid promoter ranges from 10 to 500 mg per kg of solution.

30. The process according to claim 4, wherein in the gaseous stream (ii) the concentration of hydrogen ranges from 2% to 4% by volume and the concentration of oxygen ranges from 6% to 18% by volume, the complement to 100 being an inert gas selected from nitrogen, helium and argon.

31. The process according to claim 30, wherein the inert gas is nitrogen.

32. The process according to claim 4, wherein in the gaseous stream (ii) the oxygen can be supplied using as raw material pure or substantially pure oxygen, enriched air, containing from 21 to 90% of oxygen or air, the composition of the, stream then being brought to the desired value by the addition of a suitable concentration of inert gas.

33. The process according to claim 4, wherein the liquid stream (iii) leaving the reactor has a concentration of hydrogen peroxide ranging from 4% to 10% by weight.

34. The process according to claim 4, wherein the liquid stream (iii) is separated from the catalyst by means of filtration.

35. The process according to claim 34, wherein the filtration is carried out using filters situated inside the reactor or externally by means of tangential filtration.

36. The process according to claim 4, wherein the gaseous stream (iv) leaving the reactor, essentially consisting of non-reacted hydrogen and oxygen and the inert gas, contains a volume concentration of hydrogen equal to or lower than 2% and a volume concentration of oxygen lower than 18%.

37. The process according to claim 36, wherein in gaseous stream (iv) leaving the reactor, contains a volume concentration of hydrogen ranging from 0.5 to 1.5% by volume and a volume concentration of oxygen ranging from 6 to 12%.

38. The process according to claim 4, wherein the gaseous stream (iv) leaving the reactor is recycled to the feeding to the reactor, after flushing from the system the fraction necessary for eliminating the quantity of inert gas charged in excess with the feeding and the addition of $H_2$ and $O_2$ used up in the process.

39. The process according to claim 4, wherein the gaseous stream (iv) leaving the reactor is fed to one or more subsequent reactors operating analogously to that described in claim 4, after adding each time a quantity of hydrogen and oxygen essentially equal to that used up by the reaction which takes place in the single reactors.

40. The process according to claim 4, wherein the reaction is carried out at a temperature ranging from −10 to 60° C.

41. The process according to claim 40, wherein the temperature ranges from 0 to 40° C.

42. The process according to claim 4, wherein the reaction is carried out at a total pressure ranging from 1 to 300 bars.

43. The process according to claim 42, wherein the total pressure ranges from 40 to 150 bars.

44. The process according to claim 4, wherein the reactor is a reactor suitable for operating in continuous and carrying out the reaction in a triphasic system, obtaining an effective contact between gaseous phase, liquid phase and the catalyst kept in suspension.

45. The process according to claim 4, wherein the reactor is selected from stirred reactors, bubble reactors or gas-lift reactors with internal or external circulation.

46. The process according to claim 4, wherein the residence time of the liquid medium in the reactor ranges from 0.05 to 5 hours.

47. The process according to claim 46, wherein the residence time of the liquid medium in the reactor ranges from 0.1 to 2 hours.

48. The process according to claim 1, wherein step (b) for the production of epoxides comprises:
(1) feeding the liquid stream (iii) leaving step (a) to a reaction unit consisting of one or more reactors containing the epoxidation catalyst suspended in the reaction solvent together with the olefin, hydrogen peroxide and a buffering agent;
(2) feeding the filtered liquid product leaving the reaction unit is fed to a distillation unit consisting of one or more stripping (flash) columns, one for each reactor of the reaction unit, to obtain a product at the head essentially consisting of olefin oxide and non-reacted olefin and a product at the bottom essentially consisting of solvent, non-reacted hydrogen peroxide, water and reaction by-products;
(3) feeding the product at the bottom of the distillation unit to a decomposition unit R4 consisting of one or more reactors situated in series containing a supported decomposition catalyst having the function of decomposing the residual hydrogen peroxide into $O_2$ and $H_2O$;
(4) feeding the mixture leaving the decomposition unit R4, essentially consisting of solvent, oxygen and water, together with an inert gas to a phase separator V4 to obtain, at the head, a gaseous phase containing oxygen, inert gas and traces of solvent and, at the bottom, a liquid phase consisting of solvent, water and reaction by-products;
(5) feeding the gaseous phase leaving V4 to a condensation system consisting of one or more condensers in series for the recovery of the residual solvent, whereas the non-condensable compounds (oxygen and inert gas with traces of solvent) are discharged;
(6) feeding the solvent leaving the condensation system and the liquid phase leaving V4 to the distillation column C6-A to obtain, at the head, the solvent which is recycled to the reaction unit (a), and a product, at the bottom, essentially consisting of reaction water and that charged with the hydrogen peroxide, reaction by-products and traces of solvent, which is discharged;
(7) feeding the product at the head of the stripping column(s) together with the vent products of the reactors to a distillation column C4 to obtain a product, at the head, consisting of non-reacted olefin, recycled to the reaction unit, and a product, at the bottom essentially consisting of olefin oxide;
(8) feeding the product at the bottom of the distillation column C4 to a purification system C5 to recover the residual olefin, recycled to the reaction unit, a liquid phase essentially consisting of solvent, recycled to the flash column(s), and the olefin oxide with a commercial purity.

49. The process according to claim 48, wherein in step (6) the solvent leaving the condensation system and the liquid phase leaving R4 are fed to the distillation column C6-A together with a diluted aqueous or hydro-alcoholic solution containing 10–50 mg/kg of sulfuric acid with respect to the total stream.

50. The process according to claim 49, wherein the solvent leaving the condensation system and the liquid phase leaving V4 are fed towards the bottom of the distillation column C6-A, whereas the acid solution is fed to a height equal to about ⅔ of the column itself.

51. The process according to claim 49, wherein the solvent leaving the head of the column C6-A is fed to a column C6-B, in order to separate the light products at the head, whereas the purified solvent is separated at the bottom.

52. The process according to claim 51, wherein the stream at the head of the column C6-B is sent to a distillation column C6-C, to recover, at the bottom, the solvent without light products, recycled to the hydrogen peroxide synthesis reaction, and a concentrated stream of light products, at the head.

53. The process according to claim 48, wherein in step (6) the solvent at the head of the column C6-A is recycled to the hydrogen peroxide synthesis reaction after treatment with activated carbons, sulfonic resins or sulfonated carbons.

54. The process according to claim 48, wherein the reaction unit consists of three reactors R1, R2 and R3.

55. The process according to claim 1, wherein in step (b) the olefin is selected from those having general formula (I)

wherein: $R_1$, $R_2$, $R_3$ and $R_4$, the same or different, can be hydrogen, an alkyl radical with from 1 to 20 carbon atoms, an aryl radical, alkylaryl radical with from 7 to 20 carbon atoms, a cyclo-alkyl radical with from 6 to 10 carbon atoms, an alkylcyclo-alkyl radical with from 7 to 20 carbon atoms.

56. The process according to claim 55, wherein in the compounds having formula (I), the radicals $R_1$, $R_2$, $R_3$ and $R_4$, can form, in pairs, saturated or unsaturated rings and can contain halogen atoms, nitro, nitrile, sulfonic and relative ester groups, carbonyl, hydroxyl, carboxyl, thiol, amine and ether groups.

57. The process according to claim 55, wherein olefins having formula (I) are: ethylene, propylene, allyl chloride, allyl alcohol, butenes, pentenes, hexenes, heptenes, octene-1, 1-tridecene, mesityl oxide, isoprene, cyclo-octene, cyclo-hexene or bicyclic compounds such as norbornenes, pinenes.

58. The process according to claim 57, wherein the olefin is propylene.

59. The process according to claim 58, wherein the propylene has a purity of over 70%.

60. The process according to claim 59, wherein the propylene is available as a stream from steam cracking with a minimum purity of 96%, the remainder consisting of propane and typical $C_3$ impurities.

61. The process according to claim 48, wherein the olefin fed to the reaction unit consists of fresh olefin, recycled olefin or their mixtures.

62. The process according to claim 61, wherein, before entering the reaction unit, the fresh olefin is purified in the distillation column C4.

63. The process according to claim 48, wherein the liquid stream (iii) is fed to step (1) so as to have a molar ratio olefin/$H_2O_2$ ranging from 10:1 to 1:10.

64. The process according to claim 63, wherein the molar ratio olefin/$H_2O_2$ ranges from 6:1 to 1:1.

65. The process according to claim 48, wherein the solvent used in the epoxidation reaction consists of an alcohol or mixture of $C_1$–$C_4$ alcohols or a mixture of said alcohols with water with an alcoholic content higher than 50%.

66. The process according to claim 65, wherein the alcohol is methanol.

67. The process according to claim 65, wherein the mixture is a mixture of methanol and water containing at least 70% by weight of methanol.

68. The process according to claim 48, wherein the buffering agent is selected from ammonia, ammonium acetate, ammonium formiate or a system consisting of a nitrogenated base and a salt thereof with an organic or inorganic acid.

69. The process according to claim 48, wherein the buffering agent is fed in continuous with one of the reagent streams fed to the epoxidation reactor, in such a quantity as to maintain the pH of the reaction mixture, measured under operative conditions, at a value higher than 5.

70. The process according to claim 69, wherein the pH of the reaction mixture is maintained at a value ranging from 5.5 to 8.

71. The process according to claim 1, wherein the epoxidation catalyst of step (b) is selected from titanium-silicalites with an MFI structure, titanium-silicalites with a MEL or intermediate MFI/MEL structure or beta zeolites containing titanium and having a BEA structure.

72. The process according to claim 71, wherein the catalyst is selected from titanium-silicalites having general formula (II):

$$xTiO_2 \cdot (1-x)SiO_2$$

wherein x ranges from 0.0001 to 0.04.

73. The process according to claim 72, wherein in the titanium silicalite, part of the titanium is substituted by metals selected from boron, aluminum, iron or gallium.

74. The process according to claim 1, wherein the catalyst can be used in the form of powder, pellets, microspheres, extruded or other convenient physical forms.

75. The process according to claim 74, wherein the catalyst can be used in a combination with a ligand (co-gel) or a carrier selected from silica, alumina, silica-alumina, zeolites or activated carbon.

76. The process according to claim 1, wherein the quantity of catalyst used in the epoxidation reaction ranges from 1 to 15% by weight with respect to the reaction mixture.

77. The process according to claim 76, wherein the quantity of catalyst ranges from 4 to 10% by weight with respect to the reaction mixture.

78. The process according to claim 1, wherein the epoxidation reaction is carried out at a temperature ranging from 20 to 150° C.

79. The process according to claim 78, wherein the temperature ranges from 40 to 100° C.

80. The process according to claim 79, wherein the temperature ranges from 55 to 90° C.

81. The process according to claim 54, wherein the reactors R1 and R2 operate at a temperature of 55–75° C. and a pressure of 13 bars, and the reactor R3 operates at a temperature of 70–90° C. and a pressure of 8 bars.

82. The process according to claim 48, wherein the decomposition reaction of residual hydrogen peroxide is carried out at a temperature ranging from 80 to 90° C., with a residence time ranging from 1 to 10 minutes.

83. The process according to claim 82, wherein the residence time ranges from 2 to 5 minutes.

84. The process according to claim 48, wherein the catalysts used in the decomposition reaction of residual hydrogen peroxide consist of metals of group VIII or their oxides.

85. The process according to claim 48, wherein the epoxidation reactors are selected from stirred reactors, bubble reactors, gas-lift reactors with internal or external circulation or CSTR (Continuous Stirred Tank Reactors) or PFR (Plug Flow Reactors).

86. The process according to claim 54, wherein the reactors R1, R2, R3 are of the isotherm CSTR type.

87. The process according to claim 48, wherein the decomposition reactor R4 consists of one or more fixed bed tubular reactors arranged in series.

88. The process according to claim 48, wherein the stripping columns operate under the same operating conditions and discharge, at the head, streams in vapour phase essentially consisting of non-reacted olefin, olefin oxide, inert products and solvent vapour.

89. The process according to claim 48, wherein the temperature at the bottom of the distillation column C4 does not exceed 80° C., with residence times in the order of 1 minute.

90. The process according to claim 48, wherein the purification column C5 consists of two columns in series with a high number of plates and separates, at the head, residual vapours still present, at the bottom, a liquid stream containing solvent and olefin oxide and, laterally, a liquid stream consisting of olefin oxide having a purity >99.8%.

91. The process according to claim 48, wherein the condensation heat recovered at the head of the column C6 is used to supply all the reboiling units present in the process.

* * * * *